(12) United States Patent
Royer et al.

(10) Patent No.: US 9,994,623 B2
(45) Date of Patent: Jun. 12, 2018

(54) ENTOMOTOXIC POLYPEPTIDES

(71) Applicants: INSTITUT NATIONAL DE LA RECHERCHE AGRONOMIQUE, Paris (FR); INSTITUT NATIONAL DES SCIENCES APPLIQUEES DE LYON, Villeurbanne (FR)

(72) Inventors: Corinne Royer, Sainte Foy les Lyon (FR); Pedro Da Silva, Lyons (FR); Frédéric Gressent, Chatillon sur Chalaronne (FR); Lamis Karaki, Villeurbanne (FR); Yvan Rahbe, Villeurbanne (FR)

(73) Assignees: INSTITUT NATIONAL DE LA RECHERCHE AGRONOMIQUE, Paris (FR); INSTITUT NATIONAL DES SCIENCES APPLIQUEES DE LYON, Paris (FR)

( * ) Notice: Subject to any disclaimer, the term of this patent is extended or adjusted under 35 U.S.C. 154(b) by 49 days.

(21) Appl. No.: 15/102,257

(22) PCT Filed: Dec. 9, 2014

(86) PCT No.: PCT/IB2014/066727
§ 371 (c)(1),
(2) Date: Jun. 6, 2016

(87) PCT Pub. No.: WO2015/087238
PCT Pub. Date: Jun. 18, 2015

(65) Prior Publication Data
US 2016/0297857 A1  Oct. 13, 2016

(30) Foreign Application Priority Data
Dec. 10, 2013  (FR) .................................. 13 62361

(51) Int. Cl.
C12N 15/82  (2006.01)
C07K 14/415  (2006.01)
A01N 65/20  (2009.01)

(52) U.S. Cl.
CPC ............ *C07K 14/415* (2013.01); *A01N 65/20* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 2002/0197689 A1* | 12/2002 | Corzo | .................... | A23J 1/006 435/161 |
| 2008/0086786 A1* | 4/2008 | Delobel | ................. | A01N 65/00 800/279 |
| 2012/0244575 A1 | 9/2012 | Poth et al. | | |

FOREIGN PATENT DOCUMENTS

| WO | 99/58695 A1 | 11/1999 |
|---|---|---|
| WO | 2009/056689 A1 | 5/2009 |

OTHER PUBLICATIONS

Gyorgyey et al, 2000, MPMI 13:62-71.*
Louis et al, 2004, Plant Sci. 167: 705-714.*
GenBank Accession No. AJ389043 (2011).*
Louis, S., et al., "Broad Screening of the Legume Family for Variability in Seed Insecticidal Activities and for the Occurrence of the A1b-like Knottin Peptide Entomotoxins," Phytochemistry 68:521-535, Feb. 2007.
International Search Report dated Mar. 12, 2015 issued in corresponding International Application No. PCT/IB2014/066727, filed Dec. 9, 2014, 8 pages.
Written Opinion dated Mar. 12, 2015 issued in corresponding International Application No. PCT/IB2014/066727, filed Dec. 9, 2014, 5 pages.

* cited by examiner

*Primary Examiner* — Anne Kubelik
(74) *Attorney, Agent, or Firm* — Saliwanchik, Lloyd & Eisenschenk

(57) ABSTRACT

The invention relates to novel entomotoxic polypeptides of the family of albumins 1b in legumes. Said polypeptides can be especially used as insecticides.

11 Claims, No Drawings

SEQUENCE LISTING

```
<160> NUMBER OF SEQ ID NOS: 9

<210> SEQ ID NO 1
<211> LENGTH: 41
<212> TYPE: PRT
<213> ORGANISM: Medicago truncatula

<400> SEQUENCE: 1

Ala Ser Cys Pro Asn Val Gly Ala Val Cys Ser Pro Phe Glu Thr Lys
1               5                   10                  15

Pro Cys Gly Asn Val Lys Asp Cys Arg Cys Leu Pro Trp Gly Leu Phe
            20                  25                  30

Phe Gly Thr Cys Ile Asn Pro Thr Gly
        35                  40

<210> SEQ ID NO 2
<211> LENGTH: 154
<212> TYPE: PRT
<213> ORGANISM: Medicago truncatula
<220> FEATURE:
<221> NAME/KEY: SIGNAL
```

```
<222> LOCATION: (1)..(27)
<220> FEATURE:
<221> NAME/KEY: MISC_FEATURE
<222> LOCATION: (28)..(68)
<223> OTHER INFORMATION: Mature A1b
<220> FEATURE:
<221> NAME/KEY: PROPEP
<222> LOCATION: (69)..(76)
<223> OTHER INFORMATION: A1b propeptide
<220> FEATURE:
<221> NAME/KEY: MISC_FEATURE
<222> LOCATION: (77)..(142)
<223> OTHER INFORMATION: Mature A1a
<220> FEATURE:
<221> NAME/KEY: PROPEP
<222> LOCATION: (143)..(154)
<223> OTHER INFORMATION: A1a propeptide

<400> SEQUENCE: 2

Met Thr Tyr Val Lys Leu Ala Ile Leu Ala Val Leu His Leu Thr Ile
1               5                   10                  15

Phe Leu Ile Phe Gln Thr Lys Asn Val Glu Ala Ala Ser Cys Pro Asn
            20                  25                  30

Val Gly Ala Val Cys Ser Pro Phe Glu Thr Lys Pro Cys Gly Asn Val
        35                  40                  45

Lys Asp Cys Arg Cys Leu Pro Trp Gly Leu Phe Gly Thr Cys Ile
    50                  55                  60

Asn Pro Thr Gly Ser Lys Tyr Asn Met Lys Met Ile Glu Glu His Pro
65                  70                  75                  80

Asn Leu Cys Gln Thr His Gly Glu Cys Ile Lys Lys Gly Ser Gly Asn
                85                  90                  95

Phe Cys Ala Arg Tyr Ala Asn Ala Asp Ile Glu Tyr Gly Trp Cys Phe
            100                 105                 110

Val Ser Val Ser Glu Ala Glu Arg Tyr Phe Lys Ile Gly Ser Asn Thr
        115                 120                 125

Ala Val Lys Ser Phe Phe Lys Ile Ala Ser Lys Glu Lys Asp Tyr Leu
    130                 135                 140

Lys Met Ala Leu Glu Ile Ala Thr Glu Glu
145                 150

<210> SEQ ID NO 3
<211> LENGTH: 37
<212> TYPE: PRT
<213> ORGANISM: Pisum sativum

<400> SEQUENCE: 3

Ala Ser Cys Asn Gly Val Cys Ser Pro Phe Glu Met Pro Pro Cys Gly
1               5                   10                  15

Thr Ser Ala Cys Arg Cys Ile Pro Val Gly Leu Val Ile Gly Tyr Cys
            20                  25                  30

Arg Asn Pro Ser Gly
        35

<210> SEQ ID NO 4
<211> LENGTH: 37
<212> TYPE: PRT
<213> ORGANISM: Medicago truncatula

<400> SEQUENCE: 4

Ala Asp Cys Ser Gly Ile Cys Ser Pro Phe Glu Met Pro Pro Cys Arg
1               5                   10                  15

Ser Ser Asp Cys Arg Cys Ile Pro Ile Ala Leu Ile Gly Gly Phe Cys
```

-continued

```
                 20                  25                  30

Ile Asn Pro Ile Ser
            35

<210> SEQ ID NO 5
<211> LENGTH: 37
<212> TYPE: PRT
<213> ORGANISM: Medicago truncatula

<400> SEQUENCE: 5

Asp Glu Cys Trp Gly Pro Cys Ser Val Leu Gln Thr Pro Cys Pro
1               5                   10                  15

Leu Ser Lys Cys Tyr Cys Ile Pro Leu Phe Leu Val Val Gly Tyr Cys
            20                  25                  30

Ser His Ala Ser Ser
            35

<210> SEQ ID NO 6
<211> LENGTH: 41
<212> TYPE: PRT
<213> ORGANISM: Medicago truncatula

<400> SEQUENCE: 6

Gln Ser Cys Ile Gly Phe Cys Ser Val Phe Asp Ser Lys Pro Leu Cys
1               5                   10                  15

Gly Ser Ser Arg Cys Arg Cys Asn Lys Pro Leu Asn Asn Pro Phe Val
            20                  25                  30

Gly Ile Cys Glu Arg Arg Pro Ser Thr
            35                  40

<210> SEQ ID NO 7
<211> LENGTH: 44
<212> TYPE: PRT
<213> ORGANISM: Medicago truncatula

<400> SEQUENCE: 7

Gly Gln Cys Ala Arg Val Gly Met Arg Cys Ser Arg Ala Leu Pro Asn
1               5                   10                  15

Pro Cys Gly Asp Ile Val Thr Cys Arg Cys Val His Leu His Leu Val
            20                  25                  30

Gly Ser Thr Cys Ile Asp Tyr Thr Gly Asp Gly Leu
            35                  40

<210> SEQ ID NO 8
<211> LENGTH: 41
<212> TYPE: PRT
<213> ORGANISM: Medicago truncatula

<400> SEQUENCE: 8

Glu Phe Cys Ser Ser Val Gly Ser Phe Cys Ser Pro Phe Asn Thr Asn
1               5                   10                  15

Pro Cys Gly Tyr Leu Gly Asn Cys Arg Cys Val Pro Tyr Tyr Leu Tyr
            20                  25                  30

Gly Gly Thr Cys Glu Asn Pro Phe Gly
            35                  40

<210> SEQ ID NO 9
<211> LENGTH: 40
<212> TYPE: PRT
<213> ORGANISM: Medicago truncatula
```

```
<400> SEQUENCE: 9

Ala Lys Cys Gly Glu Ala Cys Asp Thr Gln Phe Asn Phe Cys Asn Ala
1               5                   10                  15

Gly Asp Gly Cys Arg Cys Phe Ile Thr Asp Ala Tyr Leu Thr Leu Pro
            20                  25                  30

Gly Phe Cys Ala Gln Leu Ser Thr
            35              40
```

ENTOMOTOXIC POLYPEPTIDES

The present invention relates to entomotoxic polypeptides of the family of leguminous plant albumins 1b and to the uses thereof.

The albumins 1b (A1b) are entomotoxic peptides of the knottin family. These peptides were initially identified in pea seeds (Higgins et al., J. Biol. Chem., 261, 11124-30, 1986), under the name PA1b (for Pea Albumin 1 subunit b), then in soya, where they are also called leginsulin (Watanabe et al., Eur. J. Biochem., 224, 167-72, 1994), and subsequently in the seeds of other Fabaceae belonging in particular to the *Vicia, Phaseolus* and *Glycine* genera (Louis et al., Plant. Sci., 167, 705-14, 2004; Louis et al., Phytochemistry, 68, 521-35, 2007).

The sequences of the A1b peptides are strongly conserved; they comprise in particular 11 invariant residues: 5 proline residues, and 6 cysteine residues forming 3 disulfide bridges. The tertiary structure of PA1b (Jouvensal et al., Biochemistry 42, 11915-23, 2003) comprises a node formed by the three disulfide bridges, three anti-parallel β-sheets, a loop L1 containing the conserved sequence CSPFE, and a loop L2 of which the hydrophobicity of the amino acids is conserved.

It has been observed that several isoforms of A1b can coexist in the same plant (PCT application WO 99/58695; Taylor et al., J. Agric. Food. Chem., 52, 7499-506, 2004; Taylor et al., J. Agric. Food. Chem., 52, 7491-8, 2004), thereby indicating that these peptides belong to a multigene family of which the members have slightly diverged.

A1b originates from the maturation of a polyprotein called A1 (for "Albumin 1"). A1 is composed, from the N-terminal end to the C-terminal end, of a signal peptide, of the subunit b (A1b) and of its propeptide, and of the subunit a (A1a) and of its propeptide. After endopeptidic cleavage of the signal peptide, the proprotein is trafficked into the storage protein bodies of the seed. In these vacuole-derived structures, the propeptides are removed by endopeptidases, thus releasing two mature proteins: A1b and A1a.

PCT application WO 99/58695 describes the demonstration of the entomotoxic activity of PA1b, and the use thereof as an insecticide, in particular for protecting cereal seeds with respect to grain weevils. Subsequently, it has been reported that other insects are sensitive to PA1b; these are in particular coleoptera (*Sitophilus* sp., *Harmonia axyridis*), certain diptera, and in particular mosquitoes (*Culex pipiens* and *Aedes aegyptii*), and certain species of aphids such as *Acyrthosiphon pisum*. In the lepidoptera, *Mamestra brassicae, Spodoptera frugiperda*, and *Ostrinia nubilalis* are insensitive to PA1b, whereas *Ephestia khuniella* and Sf9 cells (originated from *Spodoptera frugiperda*) are sensitive thereto (Gressent et al., J Insect Sci, 7, 1-10, 2007; Gressent et al., Toxins (Basel), 3, 1502-17, 2011). It has recently been shown that the insecticidal activity of PA1b involves the inhibition of a membrane proton pump, V-ATPase, the activity of which in the intestine is essential in insects, since it provides the energy required for nutrient absorption (Chouabe et al., J Biol Chem, 286, 36291-6, 2011).

In order to determine the residues essential to the entomotoxic activity of PA1b, Da Silva et al. (Da Silva et al., J Biol Chem, 285, 32689-94, 2010) carried out various point mutations in the sequence of the protein, in particular in the L1 and L2 loops. They thus showed that the presence of the residues phenylalanine in position 10, arginine in position 21, isoleucine in position 23 and leucine in position 27 were essential to maintaining the toxic activity.

The albumins A1b are among the rare orally active entomotoxic peptides known at the current time. They have, a priori, compared with chemical pesticides, many advantages, in particular for preserving the quality of soils and water after treatment and also for protecting the farmer (during the treatment) and the consumer.

In addition, some of the A1b-sensitive insects have a very significant economic or health impact. For example, cereal weevils are responsible for cereal losses approaching 20% worldwide, mosquitoes are the primary vectors of human and mammalian diseases worldwide and aphids are vectors of plant viruses.

Currently, the albumins A1b are principally obtained by extraction from the seeds of leguminous plants (PCT application WO 99/58695), or by peptide synthesis, followed by in vitro folding (Da Silva et al., Biopolymers, 92, 436-44, 2009). They have also been produced in recombinant form, for example in *E. coli*, as described in particular by Hanada & Hirano, Biochemistry, 43, 12105-12, 2004 in the case of leginsulin, a PA1b homolog in soya, or in the yeast *Pichia pastoris* (applications CN101082046 and CN101033465).

PA1b has also been expressed in transgenic plants, in particular in cereals, in order to protect them against weevils; thus, transgenic rice plants expressing the pea PA1b protein have been obtained (Petit, Doctoral thesis, University Montpellier II, 2006; PCT application WO 2009/056689), and it has been observed that the accumulation of PA1b in the seeds derived from these plants confers on them entomotoxic properties with respect to *S. oryzae* larvae and adults. However, the toxicity level obtained is not sufficient to allow complete protection.

The inventors have undertaken to investigate whether there are, in other leguminous plants, A1b peptides with entomotoxic properties greater than those of the reference PA1b protein from pea.

This investigation allowed them to identify, in alfalfa (*Medicago truncatula*), an A1b albumin which is approximately 10 times more active than the pea PA1b albumin.

This A1b albumin is a polypeptide of 41 amino acids corresponding to the following sequence:

```
                                          (SEQ ID NO: 1)
ASCPNVGAVCSPFETKPCGNVKDCRCLPWGLFFGTCINPTG,
``` which represents the mature form of an A1b albumin.

It is derived from the maturation of a polyprotein A1, the sequence of which is the following:

```
                                          (SEQ ID NO: 2)
MTYVKLAILAVLHLTIFLIFQTKNVEAASCPNVGAVCSPFETKPCG

NVKDCRCLPWGLFFGTCINPTGSKYNMKMIEEHPNLCQTHGECIKK

GSGNFCARYANADIEYGWCFVSVSEAERYFKIGSNTAVKSFFKIAS

KEKDYLKMALEIATEE.
```

The alignment of sequences of the *Pisum sativum* PA1b polypeptide (SEQ ID NO: 3) with the A1b polypeptide of sequence SEQ ID NO: 1 of the present invention is represented below.

```
PA1b:
ASC-N-G-VCSPFEMPPCG-TSACRCIPVGLVIGYCRNPSG

SEQ ID NO: 1:
ASCPNVGAVCSPFETKPCGNVKDCRCLPWGLFFGTCINPTG
```

The amino acid variations are underlined; the residues identified as essential to the entomotoxic activity in PA1b (Da Silva et al., 2010, mentioned above) are indicated in bold.

A subject of the present invention is the A1b polypeptide of sequence SEQ ID NO: 1.

It also encompasses A1b polypeptides derived from the SEQ ID NO: 1 peptide by amino acid substitutions conserving the hydrophobicity profile, the tertiary structure and the entomotoxic properties of the SEQ ID NO: 1 polypeptide.

Non-limiting examples of substitutions are indicated in Table I below. The entomotoxic properties of the substituted peptides can be easily verified for example by determining their affinity for the PA1b-binding site, and/or their toxicity on cultures of *Spodoptera frugiperda* Sf9 cells, as described below in the example.

TABLE I

| Position | Residue | Examples of substituents | Preferred substituents |
|---|---|---|---|
| 1 | A | | |
| 2 | S | T | |
| 3 | C | | |
| 4 | P | | |
| 5 | N | Q | |
| 6 | V | L, I, W, F | L, I, F |
| 7 | G | | |
| 8 | A | | |
| 9 | V | L, I, W, F | L, I, F |
| 10 | C | | |
| 11 | S | T | |
| 12 | P | | |
| 13 | F | V, L, I, W | V, L, I |
| 14 | E | D | |
| 15 | T | S | |
| 16 | K | R | |
| 17 | P | | |
| 18 | C | | |
| 19 | G | | |
| 20 | N | Q | |
| 21 | V | L, I, W, F | L, I, F |
| 22 | K | R | |
| 23 | D | E | |
| 24 | C | | |
| 25 | R | K | |
| 26 | C | | |
| 27 | L | V, I, W, F | V, I, F |
| 28 | P | | |
| 29 | W | V, L, I, F | |
| 30 | G | | |
| 31 | L | V, I, W, F | V, I, F |
| 32 | F | V, L, I, W | V, L, I |
| 33 | F | V, L, I, W | V, L, I |
| 34 | G | | |
| 35 | T | S | |
| 36 | C | | |
| 37 | I | V, L, W, F | V, L, F |
| 38 | N | Q | |
| 39 | P | | |
| 40 | T | S | |
| 41 | G | | |

A polypeptide in accordance with the invention can be obtained by methods known in themselves, previously used for other A1b polypeptides.

It can in particular be produced by peptide synthesis, or else by genetic engineering, by expressing a polynucleotide encoding this polypeptide in an appropriate host cell or organism.

The present invention also encompasses recombinant expression cassettes comprising a polynucleotide containing a sequence encoding a polypeptide in accordance with the invention, under the transcriptional control of an appropriate promoter.

In the expression cassettes in accordance with the invention, the sequence encoding a polypeptide in accordance with the invention, such as the SEQ ID NO: 1 polypeptide, can be used in isolated form, i.e. it is not linked to the sequence encoding the corresponding propeptide, or to the sequences encoding the Ala subunit and its propeptide. Alternatively, when this coding sequence is intended to be expressed in host cells that can perform the maturation of an A1b polypeptide, the sequence encoding its propeptide, and in addition, optionally the sequence encoding the Ala subunit and/or the sequence encoding the propeptide of said Ala subunit, can where appropriate be linked thereto.

In any event, the sequence encoding the polypeptide in accordance with the invention can also be linked to a signal peptide, which may be the endogenous signal peptide of an A1 polyprotein, or, where appropriate, a heterologous signal peptide.

For the construction of the expression cassettes in accordance with the invention, the choice of the appropriate promoter will be carried out conventionally by those skilled in the art, in particular according to the host cell or organism chosen for the expression. It may thus be a prokaryotic promoter or a eukaryotic promoter. This promoter may be constitutive, or else inducible if it is desired to preferentially express the polypeptide of interest under certain environmental conditions; likewise, in the case of expression in a host organism, a tissue-specific promoter, allowing preferential expression in certain target tissues or organs, may be used.

The expression cassettes in accordance with the invention may also comprise other elements usually employed in constructs of this type in order to improve the expression of the gene of interest, such as a transcription terminator, enhancer sequences, introns, etc.

A subject of the present invention is also a recombinant vector, resulting from the insertion of an expression cassette in accordance with the invention into a host vector.

Among the very large variety of available host vectors, the choice of the most appropriate vector will be carried out, conventionally, by those skilled in the art according to, in particular, criteria such as the host cell or organism chosen, the transformation protocol envisioned, etc.

The present invention also encompasses host cells and organisms transformed with an expression cassette in accordance with the invention.

The expression "cell or organism transformed with an expression cassette" is intended to mean herein any host cell or organism in which the genetic content has been modified by transferring said expression cassette into said cell or said organism, whatever the method of transfer that was used, and whether the genetic information provided by said cassette is integrated into the chromosomal DNA or remains extra-chromosomal.

The transformed cells in accordance with the invention may be prokaryotic or eukaryotic cells. In the case of prokaryotic cells, this may for example involve *E. coli*, agrobacteria such as *Agrobacterium tumefaciens* or *Agrobacterium rhizogenes*, or entomopathogenic or symbiotic bacteria of insects, in particular bacteria capable of colonizing the digestive tract of insects. In the case of eukaryotic cells, they may in particular be plant cells, which may be derived from dicotyledonous or monocotyledonous plants, yeast cells, or insect cells. Transformed organisms in accordance with the invention may in particular be transgenic plants.

A subject of the present invention is also the use of a polypeptide in accordance with the invention as an insecticide. The insects concerned are in particular those which are sensitive to PA1b (see Gressent et al., 2007, 2011, mentioned above). In addition, those skilled in the art can readily evaluate the sensitivity of other insects to the A1b polypeptide in accordance with the invention, by adding this polypeptide, at various doses, to the food of the insects to be tested.

In the context of this use as an insecticide, the polypeptide in accordance with the invention can be used as described in PCT application WO 99/58695.

Advantageously, it can be expressed in a transgenic plant, in order to protect said plant against insect pests.

A subject of the present invention is also a process for obtaining a transgenic plant expressing a polypeptide in accordance with the invention, characterized in that it comprises the following steps:

transformation of plant cells with an expression cassette in accordance with the invention;
regeneration of plants from the transformed cells;
selection of the plants having integrated said expression cassette into their genome.

A very large number of techniques for transforming plant germ or somatic cells (isolated, in the form of tissue or organ cultures, or of the whole plant), and for regenerating the plants, are available for implementing the present invention. The choice of the most appropriate method generally depends on the plant concerned.

By way of nonlimiting examples, mention will be made of the transformation of protoplasts in the presence of polyethylene glycol, electroporation, the use of a particle gun, cytoplasmic or nuclear microinjection, or transformation by means of *Agrobacterium*. In the case of monocotyledonous plants, transformation with *Agrobacterium tumefaciens* will preferentially be used.

A subject of the present invention is also a transgenic plant comprising in its genome at least one copy of an expression cassette in accordance with the invention.

A transgenic plant is defined herein as a transformed plant in which the exogenous genetic information provided by a transforming polynucleotide is stably integrated into the chromosomal DNA, in the form of a transgene, and can thus be transmitted to the progeny of said plant. This definition therefore also encompasses the progeny of the plants resulting from the initial transgenesis, provided that they contain in their genome a copy of the transgene.

The transgenic plants in accordance with the invention express an A1b polypeptide in accordance with the invention in the whole plant, or at least in certain tissues or organs thereof, for example the seeds. This expression confers on the tissues and organs concerned a toxicity with respect to insect pests, and therefore increases their resistance to attacks by these insects.

In order to increase their spectrum of resistance with respect to insects, transgenic plants in accordance with the invention can also comprise, where appropriate, one or more other genes encoding one or more other entomotoxins. By way of examples, mention will be made of the Cry3 toxins of *Bacillus thuringiensis*, in particular Cry3A, protease inhibitors, Vip toxins, avidin, lectins, etc.

The present invention applies to all plants which do not naturally express an A1b polypeptide in accordance with the invention, or else which do not naturally express in an organ that it is desired to protect. It is of particular interest in cereals, such as wheat, corn or rice, but can also be used in any other plant that may be attacked by insect pests sensitive to this protein. This may include in particular leguminous plants other than *Medicago truncatula*, the natural resistance of which it can reinforce; by way of examples, mention will be made of pea, bean, soya, etc.

The plant materials (protoplasts, calluses, cuttings, seeds, etc.) obtained from the transformed cells or from the transgenic plants in accordance with the invention are also part of the subject of the present invention. The invention also encompasses the products obtained from the transgenic plants in accordance with the invention, and in which an A1b polypeptide in accordance with the invention is present; these are in particular the seeds and the products derived therefrom, for example flours and semolinas.

In the context of the use as an insecticide, the A1b polypeptide in accordance with the invention can also be expressed in an entomopathogenic or non-entomopathogenic microorganism, capable of infecting the insect that it is desired to target. It may for example be bacteria (Durvasula et al., Proc Natl Acad Sci USA, 94, 3274-8, 1997; Riehle et al., Int J Parasitol, 37, 595-603, 2007; Durvasula et al., Exp Parasitol, 119, 94-8, 2008) or viruses, such as baculoviruses (Bonning & Nusawardani, Methods Mol Biol, 388, 359-66, 2007; Inceoglu et al., Adv Virus Res, 68, 323-60, 2006) or densoviruses (Ren et al., PLoS Pathog, 4, e1000135, 2008).

This embodiment is of most particular interest in the case of the use with respect to non-phytophagous insects, such as mosquitoes.

The recombinant bacteria and viruses containing an expression cassette in accordance with the invention, and the use of these bacteria and viruses as an insecticide, are also part of the subject of the present invention.

The production of recombinant baculoviruses or densoviruses in accordance with the invention can be carried out by standard methods, known in themselves (see, for example, in the case of baculoviruses: O'Reilly et al., Baculovirus Expression Vectors: A Laboratory Manual, Freeman and Cie, New York, 1994, and in the case of densoviruses: PCT WO 93/01295; PCT WO 96/14423; Bossin et al., Journal of Virology, 77, 11060-71, 2003; Carlson et al., Advances in Virus Research, Volume 68, 361-92, 2006).

In the case of viruses produced in insect cells sensitive to the A1b polypeptide in accordance with the invention (for example baculoviruses produced in Sf9 insect cells), the promoter used in the expression cassette for controlling the expression of the A1b polypeptide will preferably be a late promoter (for example the polyhedrin promoter or the p10 promoter), in order to make it possible to limit the toxic effects of this polypeptide on the insect cells used for the production of these baculoviruses.

The present invention will be understood more clearly by means of the additional description which follows, which refers to a nonlimiting example illustrating the properties of the A1b polypeptide in accordance with the invention.

EXAMPLE 1: IDENTIFICATION AND CHARACTERIZATION OF ENTOMOTOXIC ALBUMINS A1B IN *MEDICAGO TRUNCATULA*

An in silico analysis of the genomic data and ESTs of *Medicago truncatula* made it possible to identify 53 genes of the albumin A1 family. 43 of these genes contained the complete sequence of a subunit A1b.

6 of these genes were chosen, and the corresponding A1b polypeptides were chemically synthesized and folded in vitro, as previously described by Da Silva et al. (Biopolymers, 92, 436-44, 2009), in order to test their activity. The PA1b polypeptide of *Pisum sativum* was also synthesized in the same way, in order to be used as a positive control.

The aligned sequences of the polypeptides synthesized are indicated in Table II below. For the *Medicago truncatula* polypeptides, the arbitrary name used herein refers to the first and last amino acid of the sequence, followed by the number of amino acids in said sequence.

TABLE II

| Name | Sequence | SEQ ID NO: |
|------|----------|------------|
| PA1b | ASC-N-G-VCSPFEMPP-CG-TSA CRCIPVGLVIGY---CRNPSG | 3 |
| AS37 | ADC-S-G-ICSPFEMPP-CR-SSD CRCIPIALIGGF---CINPIS | 4 |
| AG41 | ASCPNVGAVCSPFETKP-CGNVKD CRCLPWGLFFGT---CINPTG | 1 |
| DS37 | DEC-W-G-PCSVLQTPP-CPLSK-CYCIPLFLVVGY---CSHASS | 5 |
| QT41 | QSC-I-G-FCSVFDSKPLCGSSR-CRCNKPLNNPFVGI-CERRPST | 6 |
| GL44 | GQCARVGMRCSRALPNP-CGDIVT CRCVHLHLVGST---CIDYTGDGL | 7 |
| EG41 | EFCSSVGSFCSPFNTNP-CGYLGN CRCVPYYLYGGT---CENPFG | 8 |
| AS40 | AKC---GEACDTQFNF--CNAGDG CRCFITDAYLTLPGFCAQLST | 9 |

These peptides were then tested for their affinity for the PA1b-binding site, and for their entomotoxic properties.

The affinity for the PA1b-binding site was determined by means of ligand binding assays using a toxin labeled with iodine $^{125}$I, as previously described (Gressent et al., Eur J Biochem, 270, 2429-35, 2003).

The entomototoxic properties were determined by evaluation of the LC50 (50% lethal concentration) on cultures of *Spodoptera frugiperda* Sf9 cells, as described by Rahioui et al. (Biochimie, 89, 1539-43, 2007). The cells were cultured at 27° C. in medium from Lonza supplemented with 5% fetal calf serum (FCS) and 0.1% gentamicin, then seeded into 96-well plates, 24 h before the experiments (15,000 cells/ wells) and exposed to increasing concentrations of synthetic peptide. After 24 h, the cell viability was determined using the Celltiter-Blue viability test (Promega), in accordance with the manufacturer's instructions. After the addition of the dye, the cells were incubated at 27° C. for 4 h. The absorbance was then measured at 570 and 600 nm using a microplate reader (MR 7000, Dynatech Laboratories Inc., USA).

The results are indicated in Table III below. "–" represents a negative result (no toxicity, or no binding in the range of concentrations tested).

TABLE III

| Peptide | Ki (nM) | LC50 (nM) |
|---------|---------|-----------|
| PA1b | 17 ± 1.1 | 79.8 ± 3.6 |
| AS37 | 15 ± 2 | 107 ± 3.2 |
| AG41 | 1.3 ± 0.6 | 5.44 ± 1.7 |
| DS37 | 694 ± 2 | — |
| QT41 | — | — |
| GL44 | — | — |
| EG41 | 72.8 ± 2.7 | 75 ± 3.1 |
| AS40 | 10.3 ± 2 | 47 ± 2.2 |

These results show that some of the peptides tested (AS37, EG41, AS40) have a toxicity comparable to that of the reference PA1b peptide, while others (DS37, QT41 and GL44) do not have entomotoxic properties. In particular, the presence of a tyrosine (Y) in place of the arginine (R) in the conserved motif CXC (DS37 vs AS37) appears to correlate to a loss of binding properties and of toxicity.

The AG41 peptide has a very high toxicity, close to ten times higher than that of PA1b.

For most of the peptides (with the exception of EG41), the toxicity appears to correlate with the affinity for the PA1b-binding site.

The invention claimed is:

1. A recombinant expression cassette comprising a polynucleotide encoding a polypeptide comprising

ASCPNVGAVCSPFETKPCGNVKDCRCLPWGLFFGTCINPTG, (SEQ ID NO: 1)

said polynucleotide being placed under the transcriptional control of a prokaryotic promoter.

2. A recombinant vector containing the expression cassette as claimed in claim 1.

3. A transgenic plant comprising a transgene comprising a polynucleotide sequence encoding a polypeptide comprising

ASCPNVGAVCSPFETKPCGNVKDCRCLPWGLFFGTCINPTG. (SEQ ID NO: 1)

4. A genetically modified cell or virus comprising an expression cassette comprising a polynucleotide sequence encoding a polypeptide comprising

ASCPNVGAVCSPFETKPCGNVKDCRCLPWGLFFGTCINPTG. (SEQ ID NO: 1)

5. A method of controlling insects comprising contacting said insects with a genetically modified cell or virus according to claim 4.

6. A method of controlling insect damage to a plant comprising growing a transgenic plant according to claim 3, said plant expressing a polypeptide comprising

ASCPNVGAVCSPFETKPCGNVKDCRCLPWGLFFGTCINPTG (SEQ ID NO: 1)

in amounts toxic to insects.

7. The genetically modified cell or virus according to claim 4, wherein the genetically modified cell or virus is a plant cell.

8. The genetically modified cell or virus according to claim 4, wherein the genetically modified cell or virus is a virus.

9. The genetically modified cell or virus according to claim 4, wherein the genetically modified cell or virus is a bacterial cell.

10. The method according to claim 5, wherein the insects are contacted with a genetically modified bacterial cell.

11. The method according to claim 5, wherein the insects are contacted with a genetically modified virus.

* * * * *